United States Patent [19]

Weeks

[11] Plant 4,008

[45] Jan. 4, 1977

[54] ROSE PLANT

[76] Inventor: O. L. Weeks, 926 W. Philadelphia, Ontario, Calif. 91761

[21] Appl. No.: 671,272

[22] Filed: Mar. 29, 1976

[51] Int. Cl.[2] ..... A01H 5/00

[52] U.S. Cl. ..... Plt./12

[58] Field of Search ..... Plt./11-12, Plt./22

*Primary Examiner*—Robert E. Bagwill

*Attorney, Agent, or Firm*—Frank B. Robb

CLAIM

A new and distinct variety of rose plant of the hybrid tea class, substantially as herein shown and described, characterized particularly as to novelty by the unique combination of an extremely vigorous habit of growth; production of large flowers of exhibition form and which are mostly borne singly on exceptionally long stems; a distinctive and attractive pink and white flower color blend; and a strong flower fragrance.

1 Drawing Figure

1

The present invention relates to a new and distinct variety of Rose plant of the hybrid tea class, which was originated by me by crossing the rose variety known as "Mexicana" (U.S. Plant Pat. No. 2636) with the rose variety known as "Tiffany" (U.S. Plant Pat. No. 1304), the former being the seed parent and the latter being the pollen parent.

As the result of this breeding, I have produced a new and improved rose variety which is distinguished from its parents, as well as from all other rose varieties of which I am aware, as evidenced by the following unique combination of principal characteristics which are outstanding in the new variety:

1. An extremely vigorous habit of growth;

2. Production of large flowers of exhibition form and which are mostly borne singly on exceptionally long stems;

3. A distinctive and attractive pink and white flower color blend; and

4. A strong flower fragrance.

In comparison with the seed parent ("Mexicana") the new variety is more upright and more vigorous in its habit of growth, and the pink and white flower colors are more blending than the distinctively separate red and yellow bi-colors of this parent.

As compared with the pollen parent ("Tiffany"), the new variety is more vigorous, and there is more depth to the flower petals, with their pink color blending with white as the contrasting color, while the flowers of the parent are essentially pink which shades to creamy yellow at the base of the petals.

Asexual reproduction of my new variety by budding, as performed by me at Chino, Calif., shows that the aforementioned characteristics and distinctions come true to form and are established and transmitted through succeeding propagations.

The accompanying drawing shows typical specimens of the vegetative growth and flowers of my new rose variety in different stages of development and as depicted in color as nearly true as it is reasonably possible to make the same in a color illustration of this character.

The following is a detailed description of my new variety, with color terminology in accordance with Munsell's Color Cascade, published by Munsell Color Company, Inc., of Baltimore, Md., except where general color terms of ordinary dictionary significance are obvious:

2

Type: Hardy; outdoor; seedling; for cut flowers and for garden decoration.

Class: Hybrid tea.

Breeding: Seedling.

*Seed parent.*—"Mexicana".

*Pollen parent.*—"Tiffany".

Propagation: Holds its distinguishing characteristics through succeeding propagations by budding.

FLOWERS

Locality where grown and observed: Chino, Calif.

Flowers borne: Singly, but sometimes two or three to stem; in regular, mostly rounded clusters; on normally strong stems of medium to long length.

Quantity of bloom: Free.

Continuity: One season; from intermittent to continuous.

Fragrance: Strong.

Bud:

*Peduncle.*—Long; from medium to heavy caliper; erect; fairly smooth; with average number of light brown hairs and prickles. Color—Light grey-green.

*Before calyx breaks.*—Size—From medium to small. Form—Globular, with pointed top; with a conspicuous neck; with small foliaceous appendages on the surface of the bud; with stout, bristle-like foliaceous parts extending beyond the tip of the bud equal to ½ or more of its length. Color—Olive green, with sepals having a tint of red.

*As petals first open.*—Size—Medium. Form.— Medium length, with flat top; orbicular. Color—Outside—Creamy white, with the base blending upward into varying shades of light Pink, 41-4 to 41-7, with medium dark pink around edges. Inside—Base is pale yellow 25-3 blending upward to pale Pink and further upward to a reddish Pink, 40-10.

*Opening.*—Opens up well.

Bloom:

*Size (when fully open).*—Medium; from 3½ inches to 4 inches.

*Petalage.*—Double; from 20 to 25 petals; arranged regularly.

*Form.*—Cupped and high-centered at first, but becoming somewhat high-centered; petals being at first very tightly cupped and rolled slightly outward, but later becoming loosely cupped and slightly rolled outward at maturity.

Petals:

*Texture.*—Moderately thick; soft.

*Appearance.*—Inside—Somewhat shiny-velvety. Outside—Velvety.

*Shape.*—Outside—Orbicular; very lightly scalloped; with apex flat: Intermediate—Orbicular; lightly scalloped; with apex flat. Inside—Orbicular; with apex almost flat.

This description of a newly opened flower was made from a rose grown outdoors during the month of September at Ontario, Calif.:

*Color.*—Outer petal—Outside surface—Small segment of Yellow, 25-3, blending up to a pale Yellow, 25-1, with streaks of Pink, 41-4 at the outer edge. Inside surface—A blend of pale Yellow between a 25-4 and a 25-2, blending upward into a soft Pink between a 39-5 and a 39-7. Intermediate petal—Outside surface—Small segment of brilliant Yellow 25-3 at the base, blending upward to a soft Yellow, 25-2, further blending into a medium flesh tone with edges of a soft Pink 41-5. Inside surface—Base is medium Yellow 25-5, blending upward to a reddish Pink 40-7. Inner petal—Outside surface—Base is a medium to soft Yellow between a 25-4 and 25-2, blending upward to a soft Pink, 39-4, with a more distinct Pink on outer edges of petal. Inside surface—Base generally a medium Yellow, 25-5, blending upward rapidly to a reddish Pink, 40-7.

This description was made from a rose that was open for three days outdoors during the month of September at Ontario, Calif.:

*Color.*—Outer petal—Outside surface—Small segment of medium Yellow 25-2 at the base, blending upward to pale Pink, 41-4, blending further into a stronger Pink, 40-8. Inside surface—Pale Yellowish blend between 25-2 and 25-3 at the base, blending gradually upward into a Pink ending at the tip of reddish Pink, 40-8. Inner petal—Outside surface—Extremely pale pink, 41-1, at the base, blending slowly upward to medium soft Pink, 41-5. Inside surface—Yellowish basal segment, 25-2, blending quickly upward to medium Pink, 40-7.

*General color effect.*—Newly opened flower—Overall reddish Pink with tones of flesh and yellowish shadings on lower half of petal. 3-days open—Essentially reddish Pink with some overtones of soft fleshy Yellow.

*Behavior.*—Drop off cleanly.

*Flower longevity.*—On bush in garden—3 or 4 days in September. Cut roses grown outdoors and kept at living room temperatures—3 or 4 days in September

REPRODUCTIVE ORGANS

Stamens: From few to medium number; arranged regularly about pistils; tucked in calyx.

Filaments: From short to medium length; most with anthers.

*Color.*—White.

Anthers: From small to medium size; open at various times.

*Color.*—Brown.

Pollen: Sparse.

*Color*—Lemon Color.

Pistils: Many.

Styles: Even; long length; medium caliper; bunched; columnar.

Stigma:

*Color.*—Yellow.

Ovaries: All enclosed in calyx.

Hips: None observed.

Sepals: Permanent.

Seeds: None observed.

PLANT

Foliage:

*Leaves.*—Compound of 3–5 leaflets; from normal number to abundant; medium size; semi-soft; leathery; semi-glossy.

*Leaflets.*—Shape—Ovate. Apex—Obtuse. Base—Round. Margin—Coarsely serrate.

*Color.*—Mature—Upper surface—Normal dark green. Under surface—Moderately yellowish green. Young (somewhat wrinkled)—Upper surface—Light yellowish green. Under surface—Light yellowish green.

*Rachis (the supporting stem of the compound leaf).*—Heavy. Upper side—Slightly grooved. Under side—Moderately smooth; slightly hairy.

*Stipules.*—Long; wide; with medium to moderately long points turning out at an angle of less than 45°.

Growth:

*Habit.*—Bushy.

*Growth.*—Vigorous.

*Canes.*—Medium caliper.

*Main stems.*—Color—Dull green. Large prickles—Several; from medium length to long; hooked downward; with oval, broad base. Color—Light muddy brown. Small prickles—Few. Color—Brown. Hairs—None.

*Branches.*—Color—Dull green. Large prickles—Several; from short to medium length; hooked downward; with short to long, broad base. Color—Light brown. Small prickles—Few. Color—Light brown. Hairs—None.

*New shoots.*—Color—Bronze-red. Large prickles—Few; medium length; hooked downward; with long, broad base. Color—Bronze-red. Small prickles—Few. Color—Reddish brown. Hairs—None.

I claim:

1. A new and distinct variety of rose plant of the hybrid tea class, substantially as herein shown and described, characterized particularly as to novelty by the unique combination of an extremely vigorous habit of growth; production of large flowers of exhibition form and which are mostly borne singly on exceptionally long stems; a distincitive and attractive pink and white flower color blend; and a strong flower fragrance.

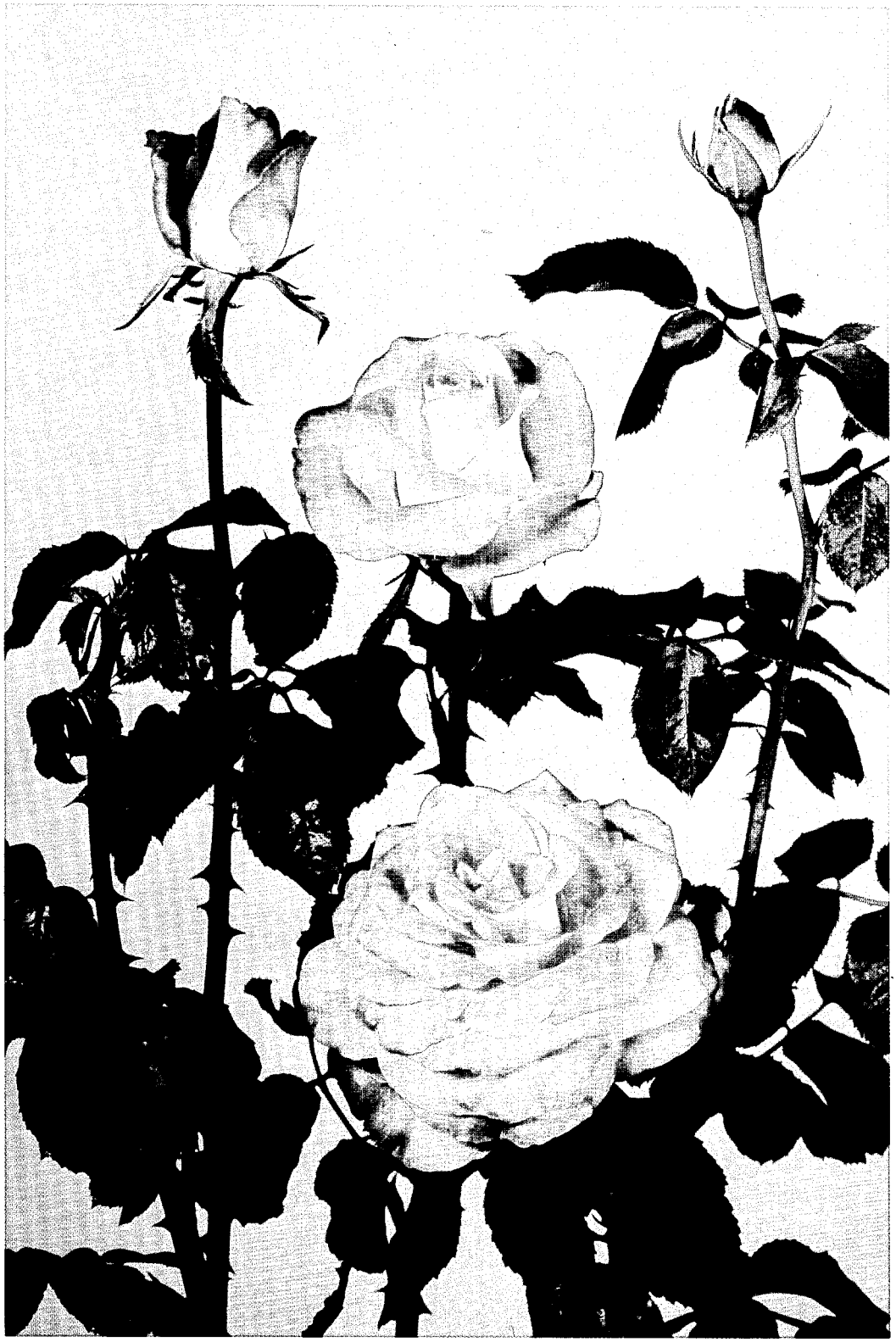

* * * * *